United States Patent
Delgado, III

(10) Patent No.: US 10,413,648 B2
(45) Date of Patent: Sep. 17, 2019

(54) METHOD AND APPARATUS FOR LONG-TERM ASSISTING A LEFT VENTRICLE TO PUMP BLOOD

(75) Inventor: Reynolds M Delgado, III, Houston, TX (US)

(73) Assignee: PROCYRION, INC., Houston, TX (US)

( * ) Notice: Subject to any disclaimer, the term of this patent is extended or adjusted under 35 U.S.C. 154(b) by 0 days.

(21) Appl. No.: 13/185,974

(22) Filed: Jul. 19, 2011

(65) Prior Publication Data

US 2012/0041255 A1 Feb. 16, 2012

Related U.S. Application Data

(63) Continuation of application No. 11/202,795, filed on Aug. 12, 2005, now Pat. No. 8,012,079.

(60) Provisional application No. 60/601,733, filed on Aug. 13, 2004, provisional application No. 60/653,015, filed on Feb. 15, 2005.

(51) Int. Cl.
*A61M 1/12* (2006.01)
*A61M 1/10* (2006.01)

(52) U.S. Cl.
CPC .......... *A61M 1/1072* (2013.01); *A61M 1/101* (2013.01); *A61M 1/1008* (2014.02); *A61M 1/1024* (2014.02); *A61M 1/122* (2014.02); *A61M 1/125* (2014.02); *A61M 1/127* (2013.01)

(58) Field of Classification Search
USPC .................................. 600/16; 623/3.13, 3.15
See application file for complete search history.

(56) References Cited

U.S. PATENT DOCUMENTS

| | | | |
|---|---|---|---|
| 4,613,329 A | 9/1986 | Bodicky | |
| 4,625,712 A * | 12/1986 | Wampler | ........................ 600/16 |
| 4,919,647 A | 4/1990 | Nash | |
| 5,147,388 A * | 9/1992 | Yamazaki | .................... 623/3.13 |
| 5,207,695 A | 5/1993 | Trout, III | |
| 5,405,383 A | 4/1995 | Barr | |
| 5,964,694 A | 10/1999 | Siess et al. | |
| 6,136,025 A | 10/2000 | Barbut et al. | |
| 6,253,769 B1 | 7/2001 | LaFontaine et al. | |
| 6,585,756 B1 | 7/2003 | Strecker | |
| 7,473,220 B2 | 1/2009 | Francese | |
| 8,012,079 B2 | 9/2011 | Delgado, III | |
| 2002/0151761 A1 | 10/2002 | Vole et al. | |
| 2003/0105383 A1 | 6/2003 | Barbut et al. | |
| 2003/0176912 A1 | 9/2003 | Chuter et al. | |

(Continued)

FOREIGN PATENT DOCUMENTS

| | | |
|---|---|---|
| WO | 200033446 | 6/2000 |
| WO | 200110342 A1 | 2/2001 |

OTHER PUBLICATIONS

International Search Report and Written Opinion, PCT/US05/028875, 16 pages.

(Continued)

*Primary Examiner* — Carl H Layno
*Assistant Examiner* — Jennifer L Ghand
(74) *Attorney, Agent, or Firm* — Winstead PC

(57) ABSTRACT

A method and apparatus for long-term assisting the left ventricle of a heart to pump blood is disclosed which includes at least one transluminally deliverable pump and a transluminally deliverable support structure which secures the at least one pump within the aorta for long-term use.

17 Claims, 7 Drawing Sheets

(56) References Cited

U.S. PATENT DOCUMENTS

| | | |
|---|---|---|
| 2003/0233143 A1 | 12/2003 | Gharib et al. |
| 2004/0044266 A1 | 3/2004 | Siess et al. |
| 2012/0172654 A1* | 7/2012 | Bates .............................. 600/16 |

OTHER PUBLICATIONS

European Search Report, EP09175307.9; dated Dec. 18, 2009.
M Herzum et al, Managing a complication after direct stenting: removal of a maldeployed stent with rotational atherectomy, Heart Jrnl 2005: 91: e46, URL: http://www.heartjnl.com/cgi/content/full/91/6/e46).
Ergun Demirsoy et al, Grafting the Restenosed Coronary Artery after Removal of Multiple Failed Stents by Endarterectomy, Texas Heart Institute Journal, Endarterectomy of Multiple Stents Before Grafts, vol. 33, No. 2, 2006, pp. 262-263.
K D Triantafyllou et al, Coronary endarterectomy and stent removal with of-pump coronary artery bypass surgery, Heart Journal, Images in Cardiology, dai: 10.1136/hrt.2005.076687, p. 885.

* cited by examiner

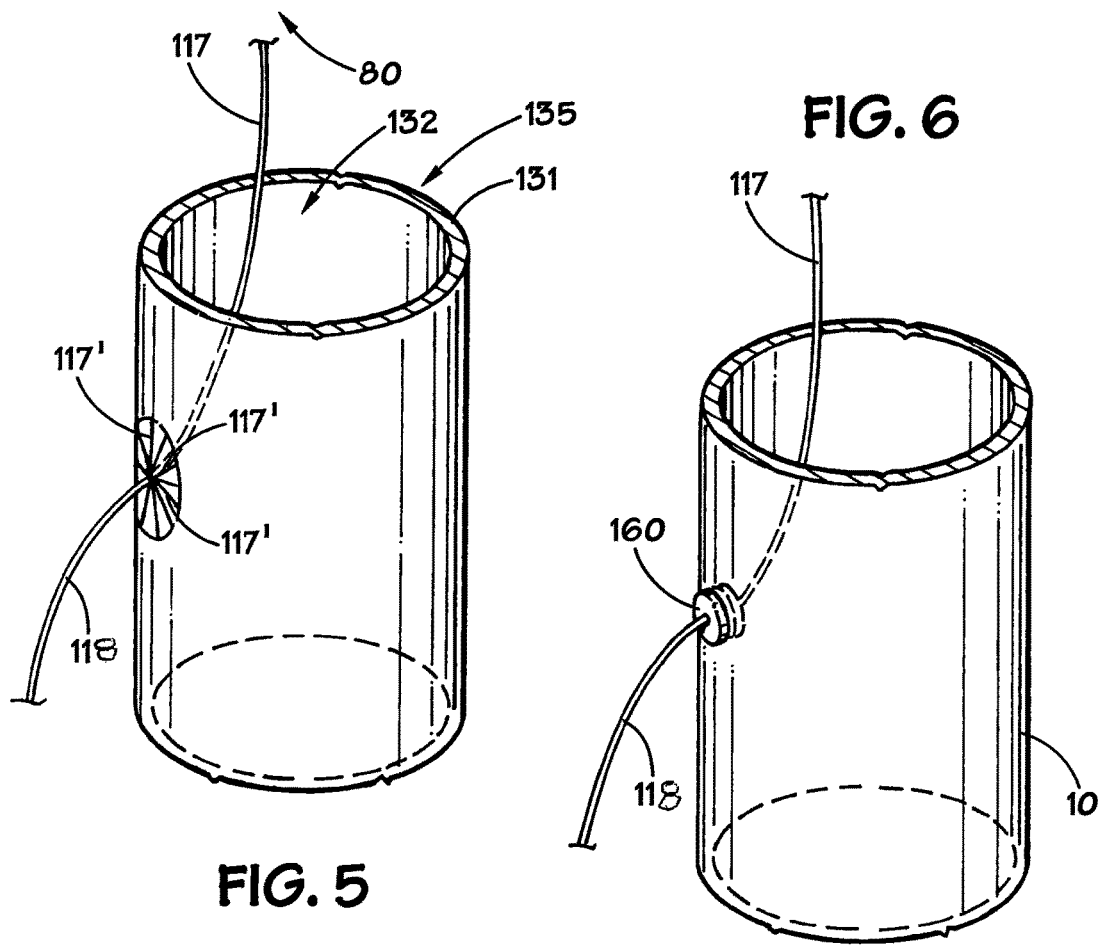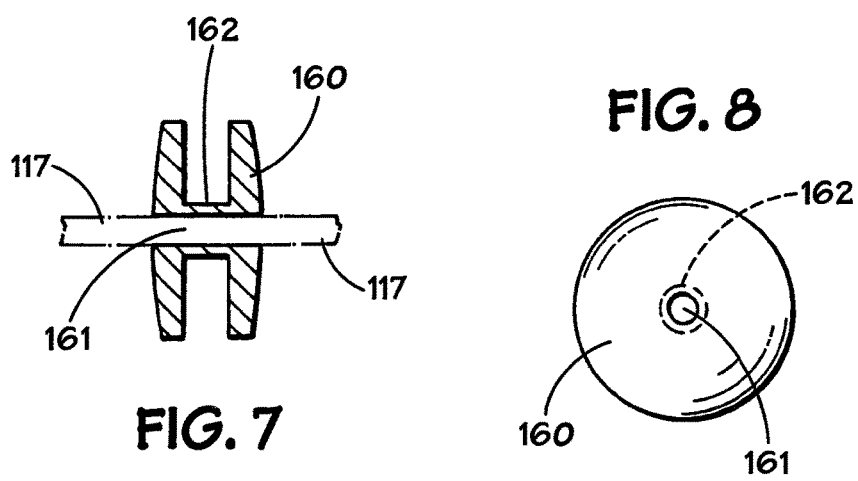

METHOD AND APPARATUS FOR LONG-TERM ASSISTING A LEFT VENTRICLE TO PUMP BLOOD

RELATED APPLICATIONS

This application is a continuation of U.S. patent application Ser. No. 11/202,795 filed on Aug. 12, 2005, now U.S. Pat. No. 8,012,079, which claims the benefit and priority of U.S. Patent Application Serial Nos. 60/601,733 filed Aug. 13, 2004, and 60/653,015 filed Feb. 15, 2005.

BACKGROUND OF THE INVENTION

Field of the Invention

The invention relates to a method and apparatus for long-term assisting the left: ventricle of a heart to pump blood. A left ventricle assist device and associated methods are disclosed.

Description of the Related Art

With the advent of new drugs, percutaneous transluminal coronary angioplasty, commonly known as "balloon angioplasty" and the use of stents in combination with balloon angioplasty, effective treatments are available for heart disease, as it relates to coronary arteries. The major problem currently in treatment of heart disease is treating individuals having congestive heart failure or who may require a heart transplant. In this regard, it is believed that only certain very ill patients may require a heart transplant, whereas many other individuals with heart disease could benefit from a less complicated, costly, and invasive procedure, provided the individual's heart can be somehow assisted in its function to pump blood through a person's body.

To this end, left ventricle assist devices ("LVAD") are in current use that can boost the heart's pumping ability, without replacing the patient's heart by way of a heart transplant. While presently available left ventricle assist devices do provide a benefit to patients with heart disease who require either a heart transplant or assistance in pumping blood throughout the body, it is believed that currently available devices have certain disadvantages associated with them. Conventional left ventricle assist devices generally require surgery upon the heart itself, including surgical incisions into the heart, which may weaken the heart, as well as requires a complicated procedure to implant the left ventricle assist device.

Most LVAD implantations require a midline sternotomy of the chest and utilization of cardiopulmonary bypass. Newer devices can be implanted through a lateral thoracotomy and can be done without using cardiopulmonary bypass; however, large loss of blood may occur during this procedure. It is also important to note the fact that all current long term LVAD devices require operation on the heart itself and disruption of the myocardium, which can lead to further problems, including arrhythmias, and left and right ventricular dysfunction, which can lead to poor outcomes in the patients. The major disadvantage in treating patients with chronic congestive heart failure through a surgical approach is that there is a significant risk of the surgery itself, including just the use of general anesthesia itself and the use of the heart lung machine. Patients with chronic congestive heart failure have impaired liver, renal, pulmonary and other organ function, and therefore, are prone to multiple complications following surgery. As a result, current long-term implantable left ventricular assist devices have a one-year mortality rate of greater than 30%.

Currently available left ventricle assist devices may include pumps placed within the left ventricle of the heart. Currently available devices typically include relatively long conduits, or fluid passageways, in fluid communication with the heart, and through which the person's blood must flow and be pumped therethrough. It is believed that the long conduits may become sites for thrombosis, or blood clots, which can possibly lead to strokes and other complications. During many of the procedures to implant such currently available devices, blood transfusions are required due to excessive bleeding by the patient. Additionally, the surgery upon the heart may lead to Right Heart Failure, which is the leading cause of early death in present patients receiving implanted left ventricle assist devices. Presently available left ventricle assist devices, which are connected to the aorta of the patient, can lead to unbalanced blood flow to certain branch vessels as compared to others. For example, the blood flow from the aorta to certain blood vessels that branch off the aorta, such as the coronary or carotid arteries, may be diminished. Lastly, present LVADs, which are implanted without chest surgery (percutaneous LVADs), are typically only used for a relatively short period of time, generally on the order of 7-10 days, whereas it would be desirable for a long-term treatment—on the order of months or even years—for patients with severe chronic congestive heart failure who cannot withstand conventional surgery.

Accordingly, prior to the development of the present invention, there has been no method and apparatus for long-term assisting the left ventricle of the heart to pump blood which: does not require surgery upon the heart itself; does not require long conduits, or fluid passageways, to connect the device to the heart; supplies a balanced and normal blood flow, or physiologic blood supply, to branch vessels, such as the coronary and carotid arteries; can be implanted without the use of general anesthesia; can be implanted and used for a long period of time; and can be transluminally delivered and implanted in a cardiac catheterization lab setting with minimal blood loss and relatively low risk of morbidity and mortality. Therefore, the art has sought a method and apparatus for long term assisting the left ventricles of the heart to pump blood, which: does not require surgery, or incisions upon the heart itself; does not require open chest surgery; does not require lengthy conduits, or fluid passageways, through which the blood must flow and be pumped through; is believed to provide a normal and balanced blood flow or physiologic blood supply, to branch vessels such as the coronary and carotid arteries; can be transluminally delivered and implanted without the use of general anesthesia; can be implanted and used for a long period of time; and can be implanted in a cardiac catheterization lab setting by a cardiologist with minimal blood loss and relatively low risk of morbidity and mortality.

SUMMARY OF THE INVENTION

In accordance with the present invention, the foregoing advantages are believed to have been achieved through the present long-term left ventricle assist device for assisting a left ventricle of a heart in pumping blood. The present invention may include a transluminally deliverable pump and a deliverable support structure, which may be implanted in the catheterization laboratory.

The method and apparatus for assisting the left ventricle of the heart to pump blood of the present invention, when compared to previously proposed methods and apparatus, is believed to have the advantages of: not requiring surgery, or incisions, upon the heart itself; not requiring the use of lengthy conduits, or fluid passageways, through which blood must pass through and be pumped through; supplying a normal and a balanced blood flow, or physiologic blood supply, to branch vessels, such as the coronary and carotid arteries; can be implanted without the use of general anesthesia; not requiring a chest surgery; can be implanted and used for a long period of time; and can be transluminally implanted in a cardiac catheterization lab setting with minimal blood loss and relatively low risk of morbidity and mortality.

BRIEF DESCRIPTION OF THE DRAWINGS

In the drawings:

FIG. 5 is perspective view of a power connection for the left ventricle assist device in accordance with the present invention;

FIG. 6 is a perspective view of another embodiment of a power connection for the left ventricle assist device in accordance with the present invention;

FIG. 7 is a side view of a connection flange in accordance with the present invention;

FIG. 8 is a front view of the connection flange of FIG. 7;

While the invention will be described in connection with the preferred embodiments shown herein, it will be understood that it is not intended to limit the invention to those embodiments. On the contrary, it is intended to cover all alternatives, modifications, and equivalents, as may be included within the spirit and the scope of the invention as defined by the appended claims.

DETAILED DESCRIPTION OF THE PREFERRED EMBODIMENTS

Figure 1:
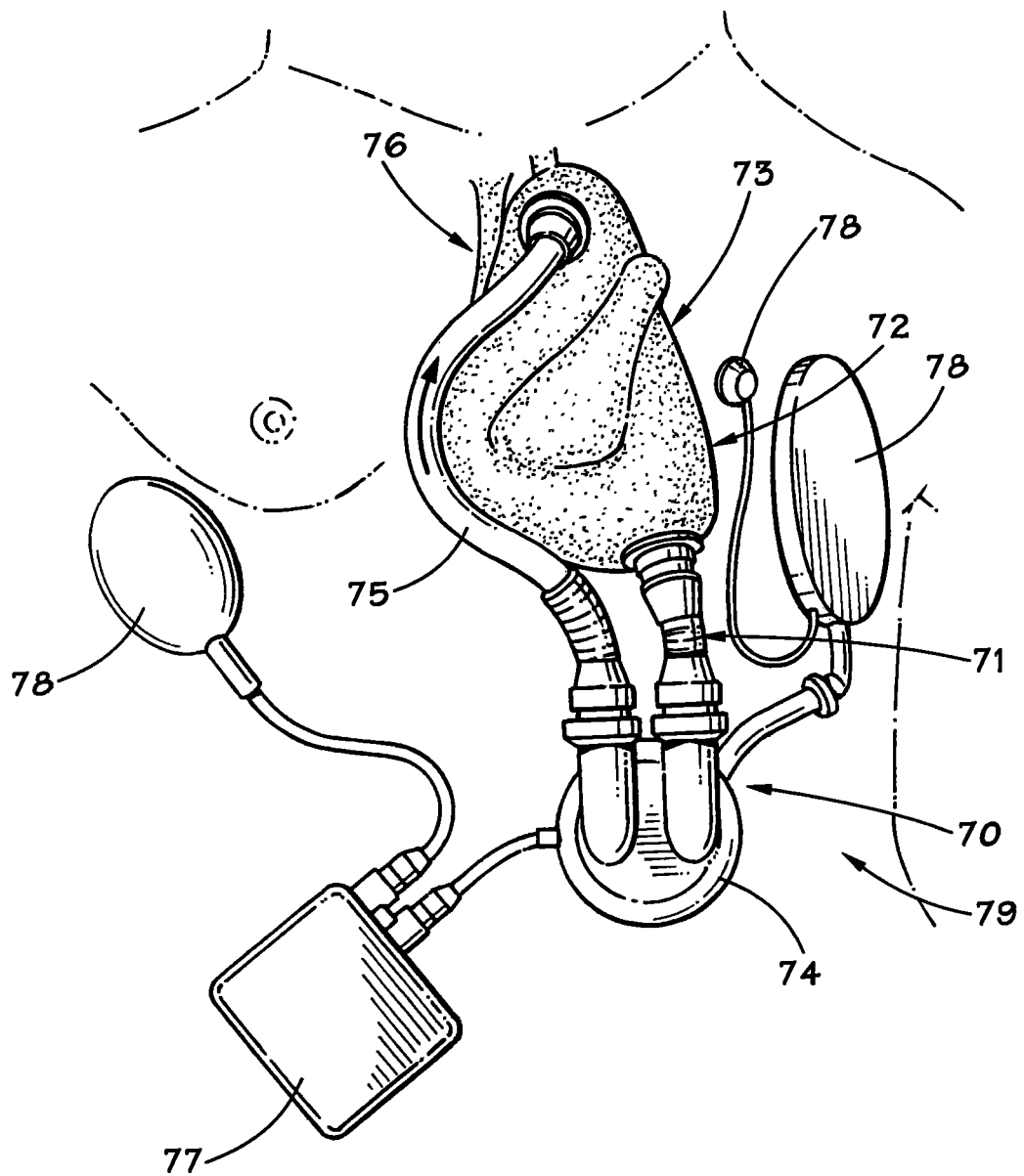
FIG. 1 is a front view of a current left ventricle assist device, illustrating its location within a patient's body.

In FIG. 1, a currently available left ventricle assist device 70 is shown to include: an inflow conduit, or fluid passageway, 71, disposed between the lower portion of the left ventricle 72 of heart 73 and a device housing 74; and an outflow conduit 75 disposed between the device housing 74 and a portion of the ascending aorta 76 of heart 73. Device 70 also includes an associated source 77 of suitable power and related sensors 78, all operatively associated with device housing 74 in a known manner.

As previously discussed, the implantation of left ventricle assist device 70 within the body 79 requires surgery incisions upon the heart 73, where the inflow conduit 71 is attached to heart 73. As also previously discussed, although left ventricle assist devices presently in use, such as device 70 illustrated in FIG. 1, do provide the best presently available level of care for patients awaiting a heart transplant, by assisting the patient's heart 73 to pump his or her blood through the patient's body, such currently available left ventricle assist devices are believed to have certain previously discussed disadvantages. These disadvantages relate to: the use of the lengthy conduits, or flow passageways, and the particularly long outflow conduit 75; and the requirement of an actual incision and surgery upon the heart muscle, including blood loss and use of general anesthesia in order to connect the inflow conduit to the left ventricle 72 of heart 73. In the regard, some devices also include implanting components thereof within left ventricle 72 of heart 73. The currently available left ventricle assist devices, such as device 70 of FIG. 1, although suffering from the previously described disadvantages, is also an acceptable device for helping patients who may not need a heart transplant, or cannot withstand the rigors of such a surgery, but who may similarly benefit from having assistance provided in pumping blood through their body.

Figure 4:
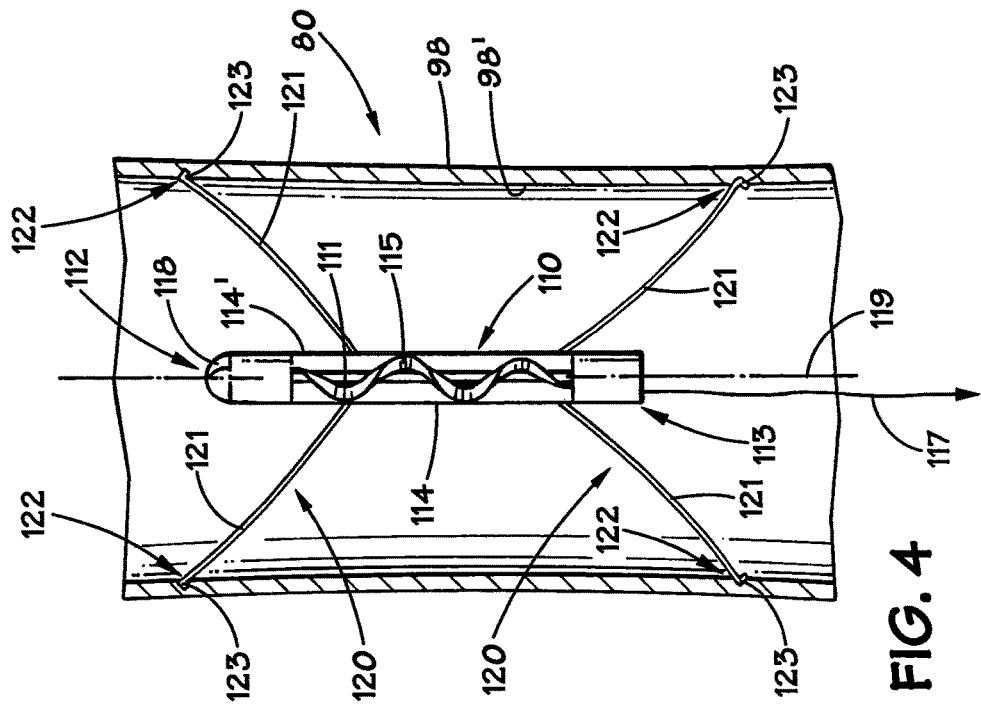
FIG. 4 is a partial cross-sectional view of the left ventricle assist device in accordance with the present invention in a second deployed configuration.
Figure 3:
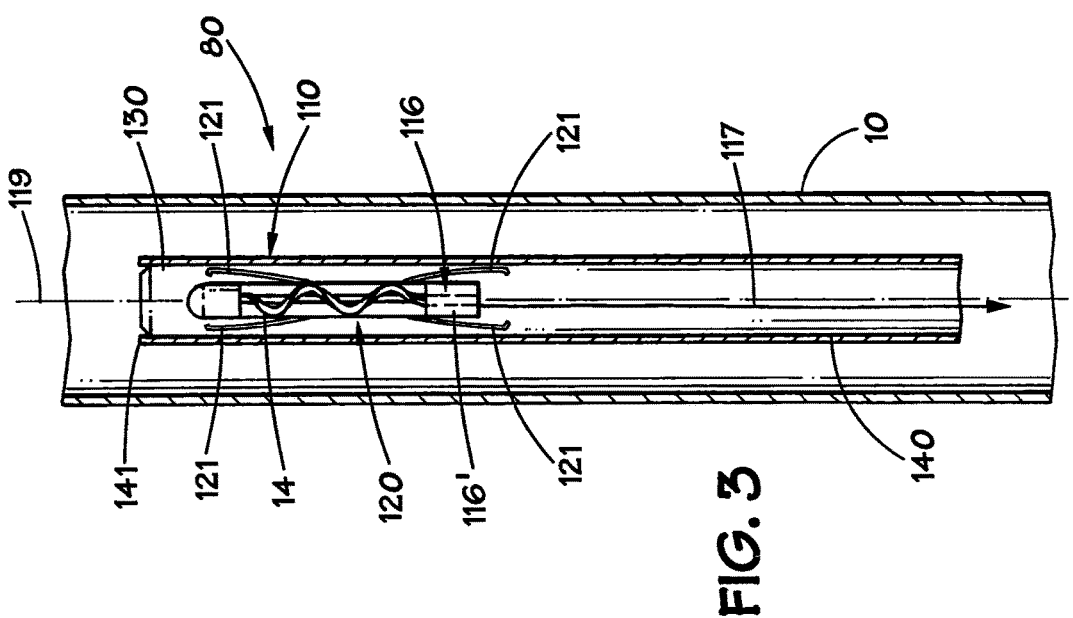
FIG. 3 is a partial cross-sectional view of the left ventricle assist device of the present invention in a first transluminal delivery configuration, the device being enlarged for clarity.

With reference to FIGS. 3-4, a left ventricle assist device 80 in accordance with the present invention is illustrated in conjunction with a patient's heart 73. Before describing the left ventricle assist device 80 of the present invention, a brief description of the functioning of heart 73 and associated arteries will help in understanding the left ventricle assist device 80 as will be hereinafter described.

In general, the heart 73 consists of two pumps lying side by side. Each pump has an upper chamber, or atrium, and a lower chamber, or ventricle, as will hereinafter be described. Heart 73 functions to provide a person's body 79 (FIG. 1) with a continuous supply of blood as illustrated by arrows 81 throughout FIGS. 2-6. In general, the right side of heart 73 receives "used" blood from the veins (not shown) of a person's body, and this blood is pumped to the lungs (not shown) of the person's body to be oxygenated. The oxygen-rich blood from the lungs is then returned to the left side of the heart, which pumps it through the various arteries. Heart 73 requires its own supply of blood to keep it beating. Oxygen-rich blood is pumped to the chambers, or ventricles, of the heart through the coronary arteries, as will be hereinafter described. Once the blood has been used, it is returned to the right side of heart 73 through a network of veins.

Figure 2:
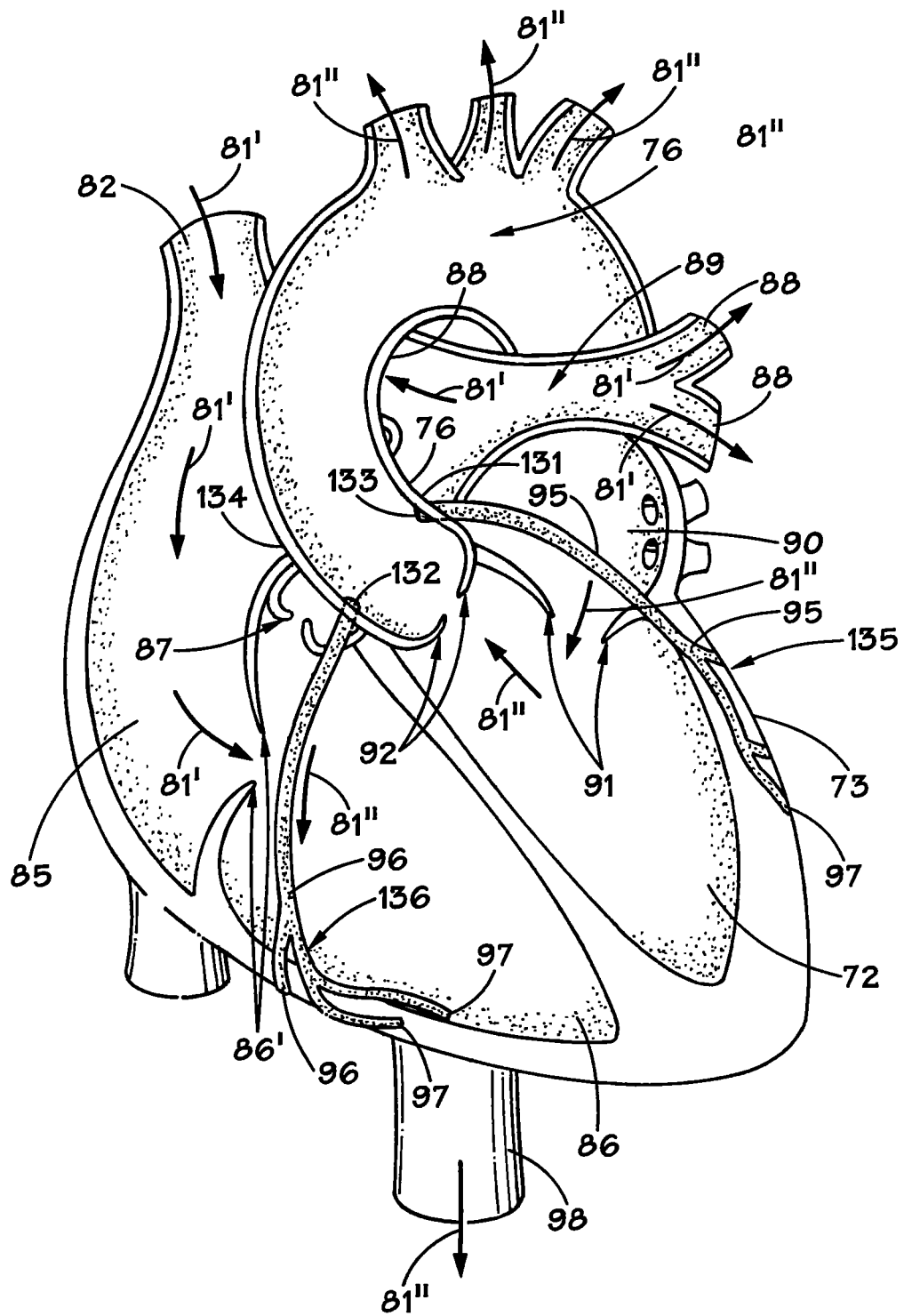
FIG. 2 is a partial cross-sectional view of a heart, to illustrate its functions and anatomy.

The functioning of these elements of heart 73 may be described in connection with FIGS. 2 and 5. Deoxygenated blood flows from veins, such as vein 82 into the right atrium, or right upper chamber, 85 of heart 73, as illustrated by arrows 81'. Deoxygenated blood 81' then flows through the one-way tricuspid valve, or right atrioventricular valve, 86' into the right lower chamber, or right ventricle, 86 of heart 73. Contraction of the muscle surrounding right ventricle 86 pumps the blood through the semilunar valve, or pulmonary valve 87, and along the pulmonary arteries 88 through the lungs (not shown), where the deoxygenated blood 81' receives oxygen. The ascending pulmonary artery is designated 89, from which pulmonary arteries 88 branch. Oxygenated blood, as represented by arrows 81" flows from the lungs into the left upper chamber, or left atrium, 90 and then passes downwardly through mitral valve, or left atrioventricular valve, 91 into the left lower chamber, or left ventricle, 72. Muscle surrounding the left ventricle 72 contracts and pumps the blood 81" through the semilunar valve, or aortic valve, 92 into the aorta, or ascending aorta, 76, and descending aorta 98. The oxygenated blood 81" is then circulated through the body's arteries and ultimately returned as deoxygenated blood 81' to the right side of heart 73 as previously described. As previously described, oxygen-rich blood 81" is pumped to the left and right sides of heart 73 through the left coronary artery 95 and right coronary artery 96. As previously described, once the oxygen-rich blood 81" has been used, the blood is returned to the right side of the heart through a network of veins 97.

With reference to FIGS. 3 and 4, the left ventricle assist device 80 of the present invention includes: a pump 110 which is percutaneously and transluminally delivered to a portion of the descending aorta 98 (FIGS. 2 and 4) of a patient 79 via the femoral artery 10 (FIG. 3) of a patient 79; and a transluminally deliverable support structure 120 which secures, or anchors, pump 110 within the descending aorta 98. Left ventricle assist device 80 is disposed within a portion of the descending aorta 98, preferably in a central portion of the descending aorta 98. Pump 110 pumps, or pulls, blood 81" downward from the ascending aorta 76, and thereafter the oxygenated blood 81" from left ventricle 72 is then circulated through the various arteries of the patient's body.

Still with reference to FIGS. 3 and 4, pump 110 is a rotary pump and preferably is an axial flow pump 111 having first and second ends 112, 113, and pump 110 is preferably disposed within a housing 114. At least one spiral vane, or impeller, 115 is disposed within housing 114. Housing 114 may be approximately 20 French diameter in size, although other sizes may be selected. Pump 110 is preferably powered by a motor 116, such as an electric motor 116', which rotates impeller 115. Impeller 115 may be mounted on bearings, or magnetically levitated, for rotation within housing 114. A power wire 117 is associated with motor 116, and as will hereinafter described in greater detail, it extends from left ventricle assist device 80 to a point at which it may be associated with a power source, such as a battery (not shown). Housing 114 may be provided with a top cover, or inflow cage, 118, which permits the passage of blood 81" into housing 114, as it is drawn into, pumped, or pulled into housing 114 by the rotation of impeller 115. Housing 114 is preferably made of a suitable metallic or plastic material, such as stainless steel, which is a bio-compatible material. Alternatively, other bio-compatible materials, including plastic materials, having the requisite strength and bio-compatibility characteristics which permit the desired use in a person's aorta may be utilized. If pump 110 is an axial flow pump 111, impeller 115 would rotate about the longitudinal axis 119 of housing 114.

Still with reference to FIGS. 3 and 4, support structure 120 of left ventricle assist device 80 includes a plurality of support members 121 associated with pump 110, which are preferably associated with housing 114. Support members 121 may be secured to the outer surface, or outer wall surface, 114' of housing 114 in any suitable manner, such as by welding or adhesive bonding. Support structure 120 supports pump 110 within the descending aorta 98, preferably in a generally, centrally spaced relationship from the interior wall surface 98' of descending aorta 98. As will be hereinafter described in greater detail, support structure 120 anchors pump 110 within descending aorta 98 for long-term use to assist the pumping of blood 81" from ascending aorta 76 downwardly through descending aorta 98. At least two support members, or struts, 121 are disposed toward the upper end 112 of pump 110 and toward the lower end 113 of pump 110. Preferably, at least three support members, or struts 121, are substantially equidistantly disposed around each of the upper and lower ends 112, 113 of pump 110. Preferably, the support members 121 have are formed of a suitable bio-compatible material, such as stainless steel. Alternatively, other bio-compatible materials, including plastic materials, having the requisite strength, expansion or spring, and bio-compatible characteristics to function in the manner hereinafter described in a person's aorta 98 may also be utilized. As shown in FIG. 3, the support structure 120, or plurality of support members 121 are disposed in a first configuration for percutaneous transluminal delivery to the desired portion of the descending aorta 98, as will be hereinafter described. In the first configuration, support members 121 are disposed substantially adjacent the outer wall surface 116 of housing 114, and are disposed substantially parallel to the longitudinal axis 119 of housing 114. In this first configuration, the overall diameter of pump 110, housing 114, and support structure 120 is reduced to permit the percutaneous transluminal delivery of the left ventricle assist device 80 through the femoral or iliac artery 10 of the patient to the desired location within the descending aorta 98.

The support members, or struts 121, may be disposed in the configuration shown in FIG. 3 as by a sheath 130 or annular bands (not shown), which may be subsequently removed, or alternatively, the struts, or support members 121, when initially attached to the outer wall surface 114' of housing 114, have the disposition shown in FIG. 3.

Upon the left ventricle assist device 80 being positioned within the desired portion of the descending aorta 98, the support members, or struts, 121, have a second, expanded configuration wherein the outer ends 122 of the support members 121 contact the inner wall surface 98' of descending aorta 98. The second disposition of the support members 121 shown in FIG. 4 may be achieved in a variety of ways. For example, the support members 121 may be formed as leaf springs, or spring members, wherein the support members 121 are biased to spring outwardly into the configuration shown in FIG. 4. If support members 121 are in the form of leaf springs which bias outwardly toward descending aorta 98, they may be initially restrained into the configuration shown in FIG. 3, by a sheath 130 or band-like member, as previously described, which may be removed when left ventricle assist device 80 has been delivered to its desired location within the descending aorta 98, whereby the support members, or struts, 121 would move outwardly into the configuration illustrated in FIG. 4. Alternatively, support members 121 could be formed of a material, such as nitinol, whereby the support members 121 would initially have the configuration shown in FIG. 3, and upon being heated by the blood flowing within aorta 98 would spring outwardly into the configuration illustrated in FIG. 4.

Figure 12:
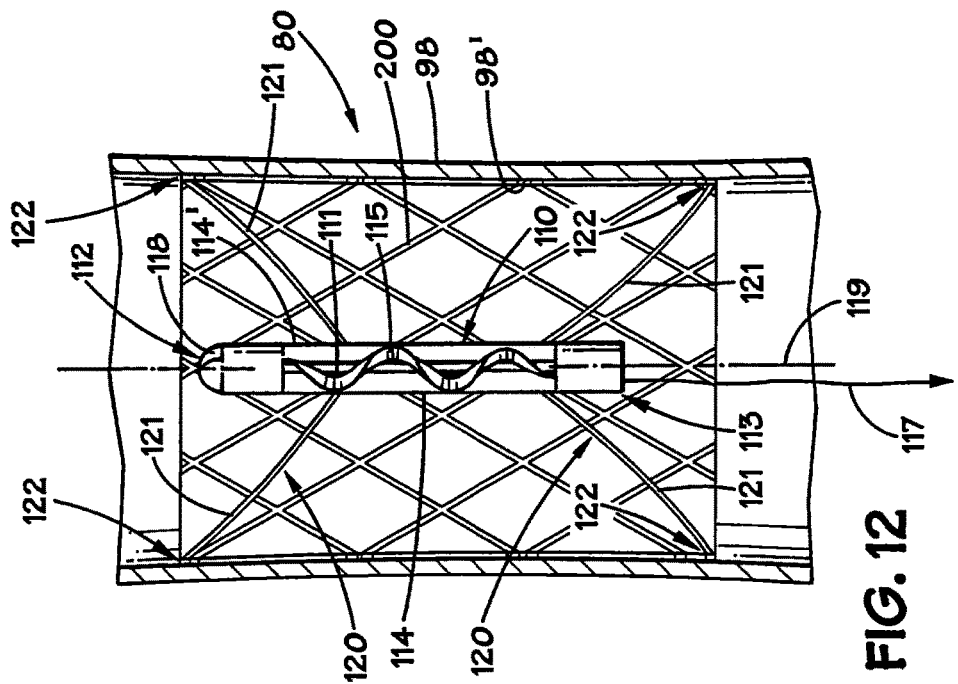
FIG. 12 is a partial cross-sectional view of another embodiment of the left ventricle assist device in accordance with the present invention in a second deployed configuration.
Figure 11:
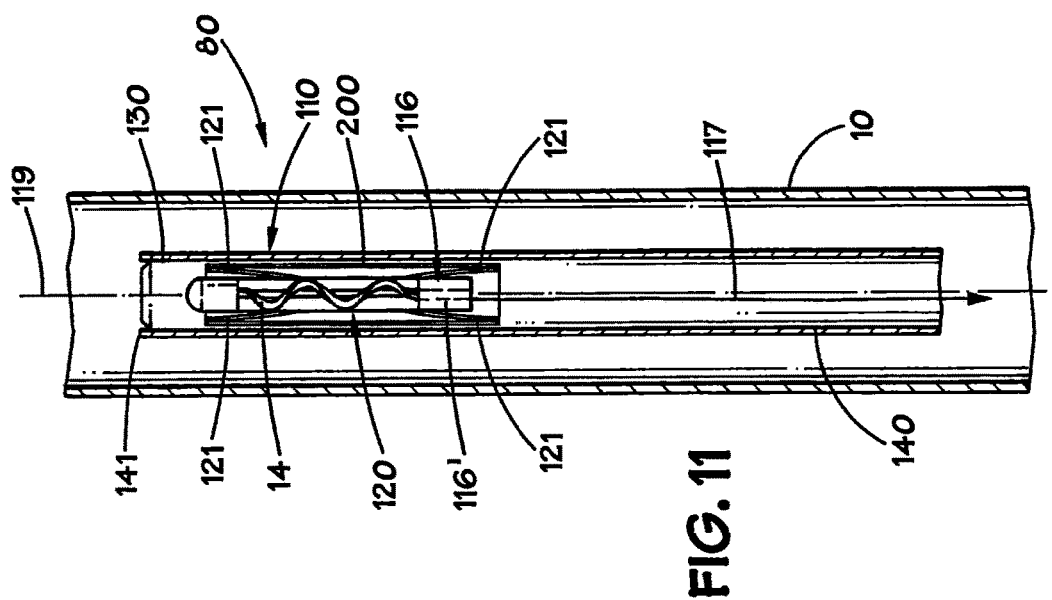
FIG. 11 is a partial cross-sectional view of another embodiment of the left ventricle assist device of the present invention in a first transluminal delivery configuration, the device being enlarged for clarity.

Other devices and structures could be utilized for support structure 120, provided they permit the percutaneous trans luminal delivery of the left ventricle assist device 80, and that after such delivery, the support structure 120 permits the disposition of the left ventricle assist device within the descending aorta for long-term use, as shown in FIG. 4. By use of the terms "long term" and "long-term use", it is meant to be more than the relatively short period of time that conventional percutaneous LVADS are used for (e.g. greater than 7-10 days, as previously described), and preferably on the order of at least a month and perhaps even a year or more. For example, a self-expanding stent 200, or stents, as are known in the art could be used for supportive structure 120, to support pump 110 in a substantially, centrally spaced relationship from the interior wall surface 98' of aorta 98, as shown in FIGS. 11 and 12. The stent, or stents, 200, schematically shown in FIGS. 11 and 12, could have pump 110 centrally disposed therein with support members, or struts 121, being attached to the interior of the stent as shown in FIG. 11. The stent 200 with the pump, and struts disposed therein, could be compressed and disposed within a sheath 130, as hereinafter discussed and transluminally delivered as seen in FIGS. 11 and 12, in a manner similar to and as shown as described with reference to FIG. 3. Upon removal of sheath 130 the self-expanding stent 200 with pump 10 and struts 121 would expand outwardly as seen in FIG. 12, similar to FIG. 4, whereby the pump 110 would be supported in a generally centrally spaced relationship from the interior wall surface 98' of aorta 98.

Figure 4A:
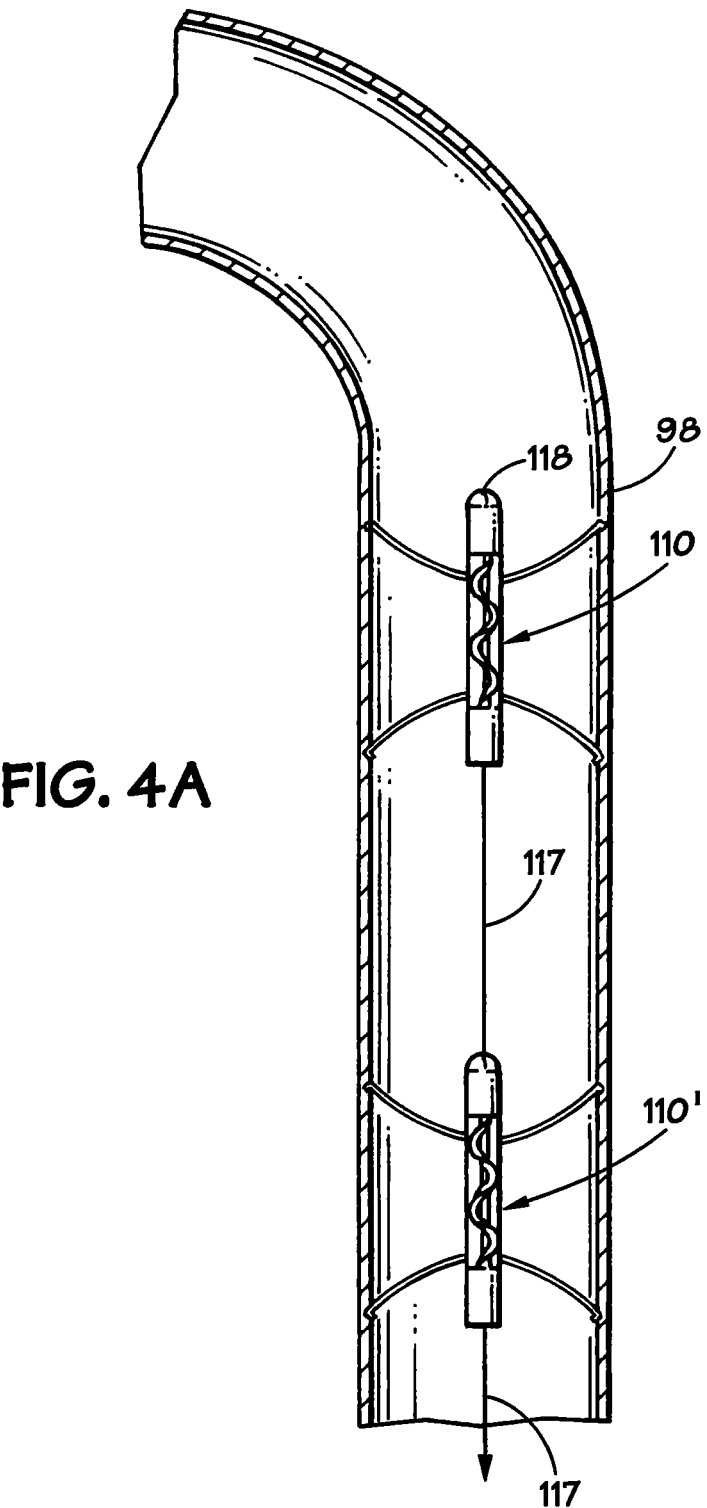
FIG. 4A is a partial cross-sectional view of another embodiment of the left ventricle assist device in accordance with the present invention in a second deployed configuration.

With reference to FIGS. 3 and 4, preferably, the outer end 122 of at least one strut 121, and preferably each of the outer ends of the support members, or struts, 121 are provided with an anchor element, such as a small hook 123, or similar structure, which serves to anchor each of the struts 121 at the desired location within descending aorta 98. If desired, a plurality of anchor elements may be used. Preferably, the left ventricle assist device 80 of the present invention is initially sheathed in a sheath 130 of approximately 22 to 23 French size in diameter in its undeployed configuration, as show in FIG. 3. If the struts 121 are of a spring-type design, the sheath 130 retains the support members 121 in the desired configuration illustrated in FIG. 3. Housing 114 preferably has a diameter of approximately 20 French. The strut system, or struts 121, may also be deployed as a separate unit from the pump and initially deployed, and thereafter the pump 110 can then be deployed into the center of the strut system utilizing a locking mechanism, so that the pump may be removed and replaced at a later date so as to allow the ability to replace the pump if it should fail. Additionally, two or more pumps 110, 110' may be placed in parallel in the descending aorta with one pump being designed in a more cranial position and the other pump in a more caudal position, so as to allow for redundancy of the pumps in case one fails and to allow for more pumping capability while utilizing the same French size sheath for delivery, as shown in FIG. 4A.

It should be apparent to one of ordinary skill in the art that other pumps 110 could be utilized in lieu of axial flow pump 111, provided pump 110 is bio-compatible and capable of operating in the environment of the body, specifically the aorta, and able to pump blood 81". Pump 110 may be powered by an implanted power device, or transformer, and may receive electric power from either an implanted power source or from a source of power located outside the patient's body 79. It should be readily apparent to one of ordinary skill that if desired other types of power could be utilized to power pump 110, such as hydraulic power or other types of power sources. The implanted power device, not shown, could be a conventional battery or a plutonium, or other nuclear material, power source.

With reference to FIG. 5, a power connection 135 for left ventricle assist device 80 is shown, with power wire 117 extending from the left ventricle assist device 80 being associated with a tubular shaped graft 131. The power wire 117 extends into the interior 132 of graft 131 and passes outwardly of the graft 131 through the wall surface of the graft 131 and includes a portion 118 of power wire 117 extending outwardly from graft 131. As will be hereinafter described in greater detail, the graft 131 is connected or anastamosed to the patient's femoral artery 10 (FIG. 3), or other suitable body passageway, and it is desirable that blood flowing within graft 131 does not leak from graft 131 at the location through which power wire 117 passes through graft 131. Graft 131 may be formed as a woven Dacron graft, as are known in the art. To provide the desired sealing about power wire 117, the individual wires 117' forming the composite power wire 117 may be woven into the interior surface of graft 131 and passed outwardly through the wall surface of the graft 131 at which point the individual wires 117 are recombined into the portion 118 of power wire 117 extending outwardly of graft 131. Graft 131 may have an approximate length of 2-3 cm. The external portion 118 of power wire 117 may then be connected to a transcutaneous energy transmission coil (not shown), which may be placed just under the skin in the patient's thigh region. The transcutaneous energy transmission coils may then receive electrical energy from another transcutaneous energy transmission coil, or antenna, worn by the patient in close proximity or remotely to the implanted transcutaneous energy transmission coil. Thus, power may be supplied to pump 110 via power wire 117. Alternatively, power wire 117 could pass through Dacron graft 131 or the vessel wall itself and a suitable bio-compatible sealant could be used to provide the requisite seal between power wire 117 and graft 131.

Alternatively, the power wire 117 could be surrounded by standard felt material, and the power wire 117 is exteriorized through the skin midway down the patient's thigh, approximate the vastous medialus or lateralus muscle. The exiting power wire 117, or portion 118, could then be connected directly to an external battery and a controller device (not shown). The controller (not shown) could be a standard power delivery device, delivering proper wattage to allow for a variable range of operation of pump 110, whereby pump 110 could pump blood at a rate of from approximately 0.5 liters/minute to as high as 5 liters/minute, depending upon the needs of the patient. The battery may be connected to the controller or incorporated within it, with one primary battery and a second auxiliary battery being utilized. The controller and batteries could be worn on the patient's belt or up on a holster-type system, or strapped to the patient's leg via a Velcro type attachment means, or other suitable attachment structure. The transcutaneous energy transmission coil could also be operated to provide varying amounts of power to pump 110 so as to also provide for the variable pumping of blood at a rate of from approximately 0.5 liters/minute to as high as 5 liters/minute.

The controller for either system could vary pump speed either in synchronization with the heart rhythm or paced rhythm, or out of synchronization with the heart rhythm or paced rhythm to provide optimal flow to the body. The device controller may also have the ability to sense the native electrocardiogram of the patient or the paced rhythm, and thus vary pump speed based upon it, and it may also communicate directly or indirectly with an implanted pacemaker, or defibrillator device, to optimize flow in this manner. The device controller may also be able to sense when the patient is supine or lying down and decrease or increase overall pump speed to compensate for decreased need while supine. The device controller may also sense other physiologic parameters such as bioimpedence, body motion or cardiac performance parameters and adjust pump speed to optimize flow of blood to the body.

The method, or procedure to transluminally implant the LVAD 80 of the present invention may include some, or all, of the following steps. First, the patient is prepared in a catheterization lab in a standard fashion. Under conscious sedation, local anesthesia is applied to the femoral area, similar to the manner in which a standard heart catheterization is performed. A small 3 cm incision is made in the vertical plane overlying the femoral artery 10, just below the inguinal ligament. The femoral artery is exposed, and may then be entered by the Seldinger technique over a guide-wire and is successively dilated to allow entry of a sheath 140, having a preferred diameter of 23 French (FIG. 3). The sheath 140 is then passed over a guide-wire and then placed into position in the descending aorta 98, with the tip 141 (FIG. 3) in the mid thoracic aorta, approximately 4 cm below the take off of the left subclavian artery. The sheath 140 is then de-aired. Sheath 140 contains at its external end, outside the patient's body, a one-way valve and a side arm for de-airing. The LV AD 80 is then passed through the one-way valve into the sheath 140 to the tip 141 at the mid thoracic area. The passage of the LVAD 80 through the sheath 140 is made possible with an obturator (not shown). As the obturator is held in place, the sheath 130 is then withdrawn, which in the case of a spring type support structure 120, the support members, or struts 121 then spring open and anchor the pump 110 in the descending aorta 98, or alternatively, if support structure 120 is a self-expanding stent 200, stent 200 springs open and anchors the pump 110 in the aorta 98. The obturator is then removed, and the sheath 140 is then pulled back with the power wire 117 still passing through, or disposed within, the sheath 140.

The graft 131 (FIG. 5) that contains the transarterial wire system, or power connection 135, is then passed through the one-way valve into the sheath 140, and the sheath 140 is successively withdrawn until the sheath exits the femoral or iliac artery. Just prior to it exiting the femoral, or iliac, artery, a clamp is placed proximal to the entry site to prevent excessive bleeding. Thereafter, a small section approximately 1.5 cm of the femoral artery is excised, and the graft 131 is anastamosed in an end-to-end fashion in an interposition technique to the femoral or iliac artery. It is then de-aired. This leaves the trans arterial wire, or portion 118 (FIG. 5) of wire 117 external to the artery 10, which is then tunneled to a drive line exit site or tunneled under the skin to a transcutaneous energy transmission coil, which is placed under the skin. The skin is then closed with suture.

Alternatively, with reference to FIGS. 6-9, after the sheath 140 is removed, a clamp is applied to prevent excessive bleeding. At the site of entry of the power wire 117 into the artery 10, a tubular graft, or a small flange member 160 is placed via a small delivery tool, which is passed over the power wire 117. The graft, or flange, 160 is put into position and the small delivery tool is removed and any excessive bleeding is observed. The flange member 160 may be made of either Dacron graft material or an inert polyurethane compound, or other biocompatible material, and flange 160 may also be a thrombin plug with a central hole 161 to allow passage of the wire 117. The flange member 160 is preferably two small, circular shaped members joined by a central portion 162, which has a central hole 161 through which the wire passes. The flange 160 is preferably 25 French in diameter, whereby it is large enough to occlude the hole in the artery 10, which was made by the large sheath 140. This flange system allows for externalization of the power wire 117 from the artery 10 without excessive bleeding while preventing formation of an arterial fistula. The power wire is now external to the artery 10 and can be attached to an internal implanted transcutaneous energy transmission coil or exteriorized through a drive line as previously described.

After access to the artery 10 is gained, anti-coagulation with a short term intravenous anti-coagulant is provided during the procedure, and immediately thereafter, until long-term oral anti-coagulation can be instituted, if needed.

Figure 9:
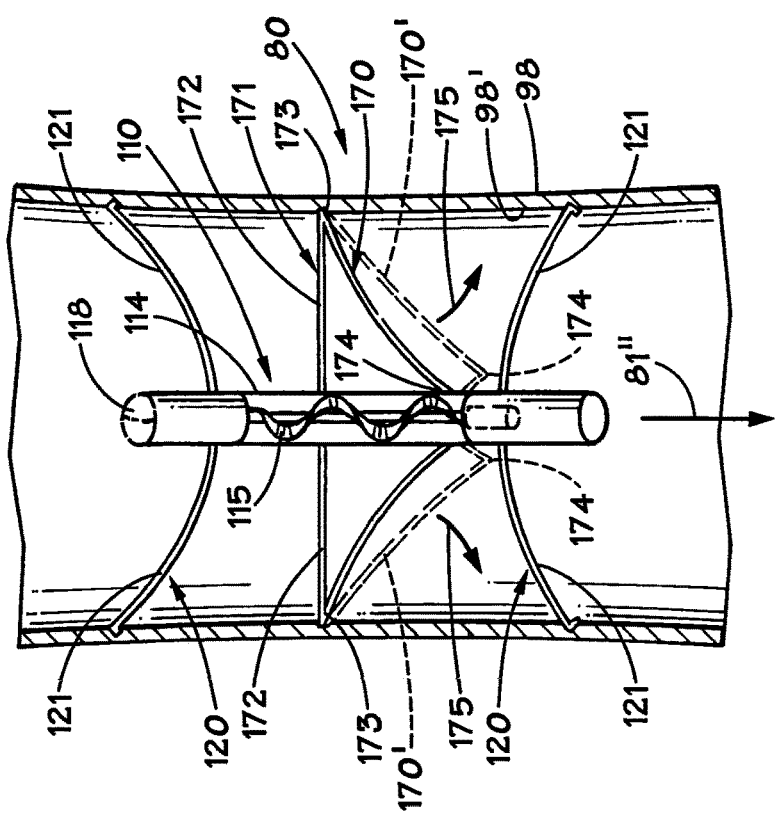
FIG. 9 is a partial cross-sectional view of an embodiment of the left ventricle assist device in accordance with the present invention, similar to that of FIGS. 3 and 4, including a one-way valve.

With reference to FIG. 9, a figure similar to FIG. 4, the left ventricle assist device 80 is provided with a one-way valve 170, and is shown disposed in the descending aorta 98. The same reference numerals are used for the same components shown and described in connection with FIGS. 3 and 4. One-way valve 170 may be provided to prevent backflow of blood 81" from flowing upwardly back into descending aorta 98. One-way valve 170 may be provided in any suitable manner, such as by supporting one-way valve 170 by a strut system 171 associated with housing 114. Strut system 171 may include a plurality of strut members 172 which may be deployed in a similar manner to strut members 121 of strut system 120 to bring the circumferential end, or lip, 172 of one-way valve 170 into a sealing relationship with the interior surface 98' of descending aorta 98. The other, smaller diameter circumferential end, or lip, 174 of one-way valve 170 is shown in FIG. 9 disposed in its sealed relationship with respect to housing 114, whereby backflow of blood 81" upwardly into descending aorta 98 is prevented. As blood 81" is pumped to flow downwardly into descending aorta 98, one-way valve 170 may open as shown by dotted lines 170', whereby one-way valve 170 opens as shown in the direction of arrows 175, whereby the circumferential lip 174 of one-way valve 170 moves outwardly from housing 114 to permit blood 81" to flow not only through pump 110, but from outside housing 114 and into descending aorta 98.

One-way valve 170 may be made of any suitable biocompatible, or biomaterial, including plastic materials, having the requisite strength and bio-compatibility characteristics which permit the desired use in a person's aorta and permits the function of one-way valve 170. Rigid biomaterials, or flexible biomaterials may be utilized for the construction of one-way valve 170.

Figure 10:
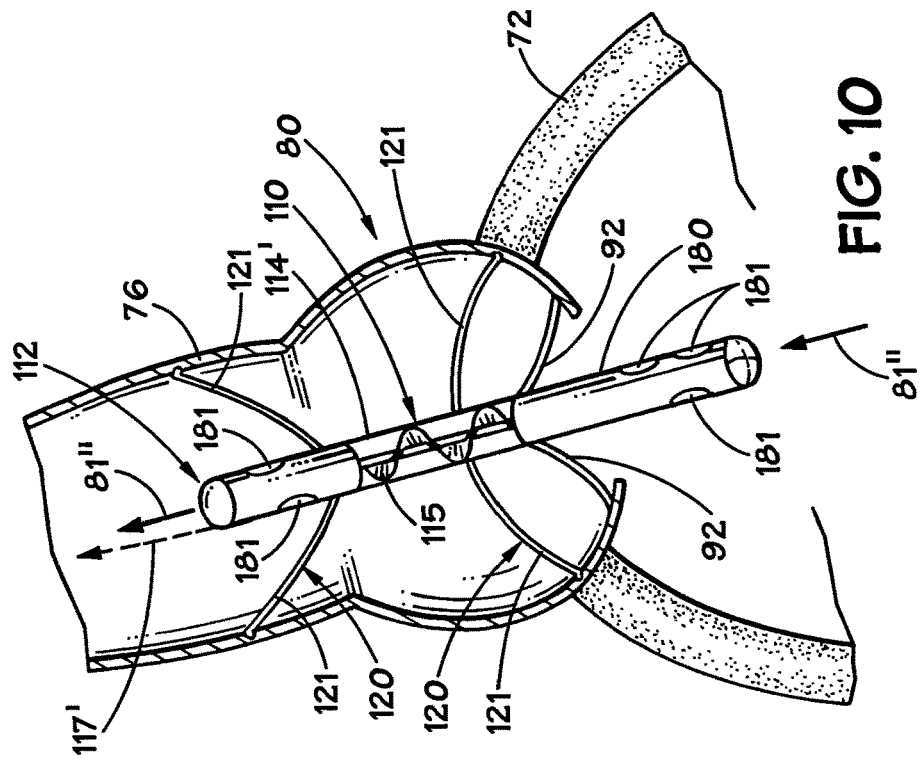
FIG. 10 is a partial cross-sectional view of the left ventricle assist device of the present invention being deployed in the ascending aorta.

With reference to FIG. 10, the left ventricle assist device 80 of the present invention, having the same general construction as illustrated in connection with FIGS. 3 and 4 is shown disposed, not in the descending aorta 98, but rather in the ascending aorta 76, with oxygenated blood 81" being pumped by pump 110 from the left ventricle 72 and outwardly into the aortic root, or ascending aorta, 76. In this embodiment of the left ventricle assist device 80, the housing 114' is lengthened to include an inflow cannula 180, which may be provided with a plurality of openings, or ports, 181 formed in the side walls of cannula 180. Similar ports 181 may also be provided in the upper end of housing 114', which ports 181 assist in the passage of blood 81" through housing 114'. As shown in FIG. 10, housing 114' is anchored within ascending aorta 76 by a plurality of strut members 121, and housing 114' is disposed within aortic valve 92. When the left ventricle assist device 80, shown in FIG. 10, is deployed within the ascending aorta 76, the aortic valve 92 functions as the one-way valve which may be provided, as discussed in connection with the embodiment of LVAD 80 of FIG. 9. It is believed that by disposing the left ventricle assist device 80 within the ascending aorta 76, direct unloading of the left ventricle 72 will be provided, so that more efficient afterload reduction may be accomplished. It is also believed that deployment of the left ventricle assist device in the ascending aorta 76 will also permit better perfusion of the cerebral circulation. In the embodiment of left ventricle assist device 80 of FIG. 10, power wire 117' may be associated with the upper, or first end, 112 of pump 110.

Alternatively, rather than transluminally implanting the LVAD 80 of the present invention through the femoral artery, as previously described, LVAD 80 may be transluminally implanted and delivered through the left or right subclavian artery, and the power source or battery and controller may be placed in the pectoral area of the patient. This type of implant technique would be similar to the implantation of a cardiac pacemaker or defibrillator, with the exception that access would be obtained through the subclavian artery, rather than the subclavian vein. The power source, and/or its controller, may be incorporated in a device such as a cardiac pacemaker or defibrillator, if used in this manner.

Alternatively, if desired, the pump 110 and support structure 120, including support members 121, could be designed whereby pump 110 and support structure 120 could be removed with a catheter based removal device (not shown) which could collapse support members 121 and disengage them from their anchored configuration to permit the removal of them and pump 110, if desired, such as to replace or repair pump 110. Such a catheter based removal device could be similar to those presently used with inferior vena cava filters.

The present invention has been described and illustrated with respect to a specific embodiment. It will be understood to those skilled in the art that changes and modifications may be made without departing from the spirit and scope of the invention as set forth in the appended claims.

I claim:

1. A blood flow assist device comprising:
    a transluminally deliverable housing implantable within a vessel, wherein the housing is biocompatible;
    at least one pump within the housing, wherein the pump provides axial blood flow;
    a plurality of struts secured to the housing, wherein the plurality of struts are collapsible to a compressed configuration that allows removal of the blood flow assist device from the vessel, expandable to an expanded configuration to secure the housing in the vessel,
    each of the plurality of struts comprise a thin, long member with
        a first tip at a first terminal end of the thin, long member adapted to be in contact with a wall of the vessel and
        a second tip at a second terminal end opposite the first terminal end of the thin, long member secured to the housing, and
    when in the expanded configuration, the plurality of struts are the only obstruction to native blood flow between an entirety of the housing and the wall of the vessel at all times; and
    a locking mechanism for securing the at least one pump to the plurality of struts, wherein the plurality of struts are a separate unit from the at least one pump, and the locking mechanism provides the capability to remove the at least one pump from the plurality of struts.

2. The blood flow assist device of claim 1, wherein at least one of the plurality of struts provides a hook at the first tip.

3. The blood flow assist device of claim 1, wherein the plurality of struts centrally dispose the pump housing in the vessel.

4. The blood flow assist device of claim 1, wherein the plurality of struts are disposed around a circumference of the at least one pump.

5. A method for providing blood flow assistance to a circulatory system, the method comprising the steps of:
    providing at least one pump which is associated with transluminally deliverable support members, wherein the support members include a plurality of struts, and the plurality of struts are collapsible to a compressed configuration that allows removal of the blood flow assist device from a vessel;
    transluminally delivering the at least one pump and the support members to a desired location within the vessel;
    placing the support members into an expanded configuration to secure the pump and the support members at the desired location,
    wherein each of the plurality of struts comprise a thin, long member with
        a first tip at a first terminal end of the thin, long member adapted to be in contact with a wall of the vessel and
        a second tip at a second terminal end opposite the first terminal end of the thin, long member secured to a housing of the at least one pump, and
    when in the expanded configuration, the plurality of struts are the only obstruction to native blood flow between an entirety of the housing and the wall of the vessel at all times;
    supplying power to the at least one pump to pump blood; and
    a locking mechanism for securing the at least one pump to the plurality of struts, wherein the plurality of struts are a separate unit from the at least one pump, and the locking mechanism provides the capability to remove the at least one pump from the plurality of struts.

6. The method of claim 5, further comprising the step of utilizing a hook at the first tip on at least one of the plurality of struts to anchor the pump and the support members in the desired location.

7. The method of claim 5, wherein the pump and the support members are disposed within a sheath and the sheath is removed to deploy the support members into the expanded configuration.

8. The method of claim 5, wherein the plurality of struts centrally dispose the pump housing in the vessel.

9. The method of claim 5, wherein the plurality of struts are disposed around a circumference of the at least one pump.

10. A blood flow assist device for assisting blood flow in a circulatory system, the device comprising:
    a transluminally deliverable housing implantable within a vessel, wherein the housing provides at least one pump to assist blood flow;
    a plurality of struts secured to the housing, wherein the plurality of struts are collapsible to a compressed configuration that allows removal of the blood flow assist device from the vessel, expandable to an expanded configuration centrally disposing the housing in the vessel,
    each of the plurality of struts comprise a thin, long member with
        a first tip at a first terminal end of the thin, long member adapted to be in contact with a wall of the vessel and
        a second tip at a second terminal end opposite the first terminal end of the thin, long member secured to the housing, and
    when in the expanded configuration, the plurality of struts are the only obstruction to native blood flow between an entirety of the housing and the wall of the vessel at all times; and a locking mechanism for securing the at least one pump to the plurality of struts, wherein the plurality of struts are a separate unit from the at least one pump, and the locking mechanism provides the capability to remove the at least one pump from the plurality of struts.

11. The blood flow assist device of claim 10, wherein at least one of the plurality of struts provides a hook at the first tip.

12. The blood flow assist device of claim 10, wherein the plurality of struts are disposed around a circumference of the at least one pump.

13. A blood flow assist device for assisting blood flow in a circulatory system, the device comprising:
- a transluminally deliverable housing implantable within a vessel, wherein the housing provides at least one pump to assist blood flow;
- a stent in contact with a wall of the vessel after deployment; and
- a plurality of struts secured to the housing, wherein the plurality of struts are collapsible to a compressed configuration that allows removal of the blood flow assist device from the vessel, expandable to an expanded configuration to secure the housing in the vessel,
- each of the plurality of struts comprise an elongated, thin member connecting a first tip adapted to be in contact with the wall of the vessel and a second tip secured to the housing, wherein at least one of the plurality of struts is attached to the stent, and
- when in the expanded configuration, the plurality of struts and the stent are the only obstruction to native blood flow between an entirety of the housing and the wall of the vessel at all times.

14. The blood flow assist device of claim 13, wherein the stent is a self-expanding stent.

15. The blood flow assist device of claim 13, wherein the plurality of struts centrally dispose the pump housing in the vessel.

16. The blood flow assist device of claim 13, wherein the plurality of struts are disposed around a circumference of the at least one pump.

17. The blood flow assist device of claim 13 further comprising:
- a locking mechanism for securing the at least one pump to the plurality of struts, wherein the plurality of struts are a separate unit from the at least one pump, and the locking mechanism provides the capability to remove the at least one pump from the plurality of struts.

* * * * *